United States Patent
Hall et al.

(10) Patent No.: US 11,992,242 B2
(45) Date of Patent: May 28, 2024

(54) SEAL CARTRIDGE LATCH DESIGN FOR TROCAR ASSEMBLIES

(71) Applicant: Cilag GmbH International, Zug (CH)

(72) Inventors: Steven G. Hall, Lebanon, OH (US); Joseph Thomas Mozloom, Jr., Cincinnati, OH (US); Katherine J. Schmid, Cincinnati, OH (US); Harry Randolph Adams, Fort Thomas, KY (US)

(73) Assignee: Cilag GmbH International, Zug (CH)

( * ) Notice: Subject to any disclaimer, the term of this patent is extended or adjusted under 35 U.S.C. 154(b) by 328 days.

(21) Appl. No.: 17/240,381

(22) Filed: Apr. 26, 2021

(65) Prior Publication Data
US 2021/0244441 A1    Aug. 12, 2021

Related U.S. Application Data

(63) Continuation of application No. 16/034,942, filed on Jul. 13, 2018, now Pat. No. 10,987,135.

(51) Int. Cl.
*A61B 17/34* (2006.01)
*A61B 17/02* (2006.01)

(52) U.S. Cl.
CPC ...... *A61B 17/3498* (2013.01); *A61B 17/0218* (2013.01); *A61B 17/3423* (2013.01)

(58) Field of Classification Search
CPC ............ A61B 17/0218; A61B 17/3423; A61B 17/3462; A61B 17/3498; A61B 17/02
See application file for complete search history.

(56) References Cited

U.S. PATENT DOCUMENTS

| | | | |
|---|---|---|---|
| 5,197,955 A * | 3/1993 | Stephens | A61B 17/3462 604/167.01 |
| 5,792,113 A | 8/1998 | Kramer | |
| 7,025,747 B2 * | 4/2006 | Smith | A61B 17/3462 606/167 |
| 8,012,128 B2 * | 9/2011 | Franer | A61B 17/3462 604/164.07 |
| 2004/0236347 A1 | 11/2004 | Karasawa | |
| 2017/0056064 A1 | 3/2017 | Zergiebel | |

FOREIGN PATENT DOCUMENTS

| | | |
|---|---|---|
| EP | 2226026 A1 | 9/2010 |
| EP | 3020347 A1 | 5/2016 |
| WO | 2012144846 A2 | 10/2012 |
| WO | 2015142794 A1 | 9/2015 |

* cited by examiner

*Primary Examiner* — Anu Ramana
(74) *Attorney, Agent, or Firm* — Vorys, Sater, Seymour and Pease LLP

(57) ABSTRACT

A trocar assembly that includes a trocar and a seal cartridge configured to be releasably coupled to the trocar. The seal cartridge includes a top cap that includes a main body and a latch ring. The latch ring is grounded to the main body at a first angular position and has a latch located at a second angular position angularly offset from the first angular position. Applying a radial load on the latch causes the latch ring to flex in torsion at an intermediate portion that angularly interposes the first and second angular positions.

20 Claims, 4 Drawing Sheets

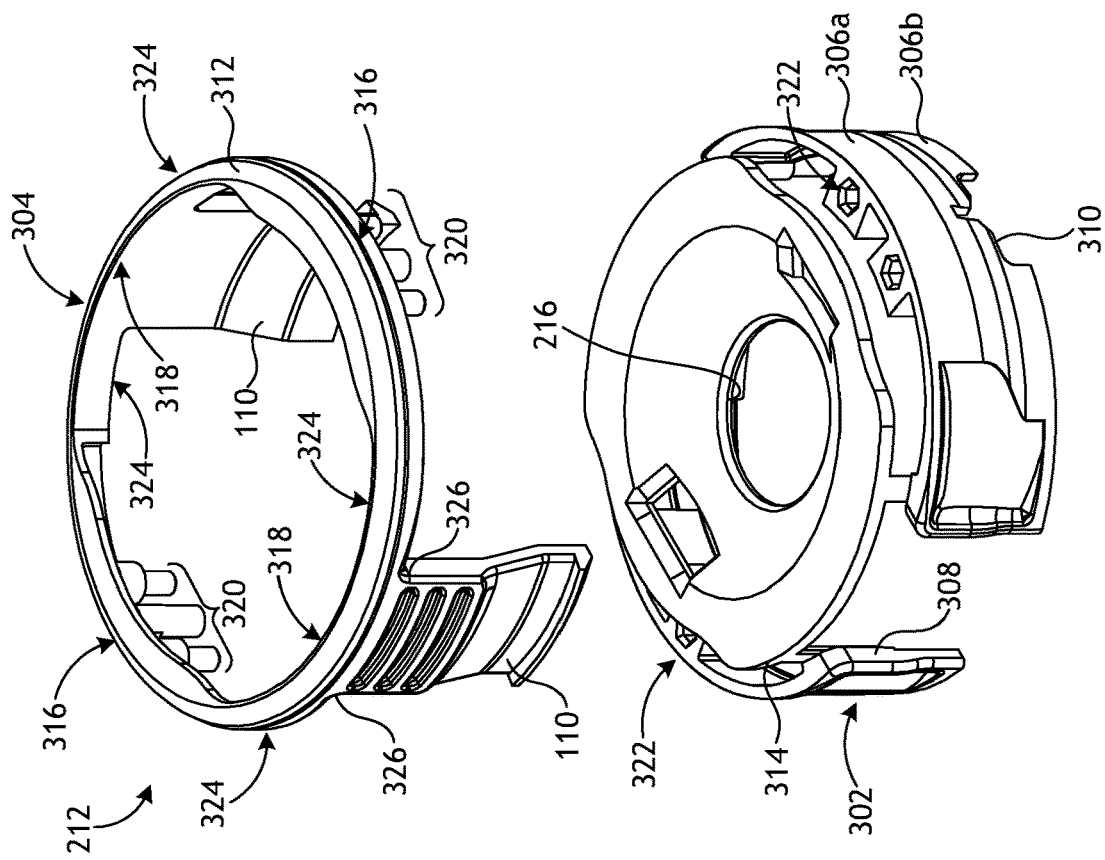
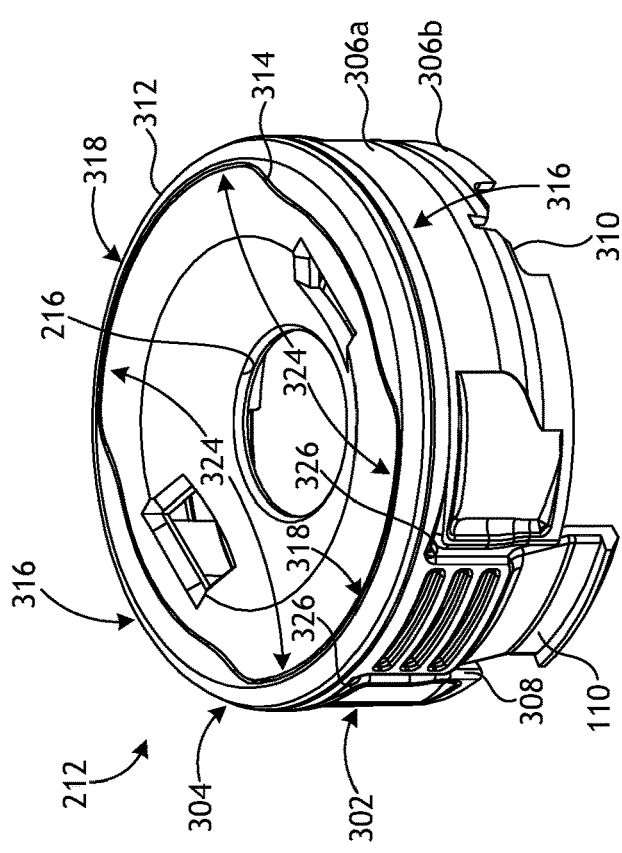
FIG. 3B
FIG. 3A

SEAL CARTRIDGE LATCH DESIGN FOR TROCAR ASSEMBLIES

BACKGROUND

During laparoscopic surgery, one or more small incisions are formed in a patient's skin and a trocar assembly is inserted through the incision to provide access to an internal body cavity, such as the patient's abdomen. The trocar assembly operates as a pathway that can be used to introduce various surgical instruments and tools into the abdomen.

A trocar assembly generally includes a trocar and a seal assembly operatively coupled to or forming part of the trocar. The trocar includes a trocar housing and a cannula that extends distally from the trocar housing and provides the pathway into the patient's abdomen. The seal assembly includes one or more seals that help maintain insufflation of the penetrated body cavity and also seal about surgical tools extended through the trocar and into the patient's abdomen.

In some applications, the seal assembly may comprise a seal cartridge at least partially received within the trocar housing and releasably coupled thereto. Due to minimal space constraints, it is desired to releasably couple the seal cartridge to the trocar housing simply and efficiently. The seal cartridge may be allowed to rotate continuously and freely within the trocar housing once releasably coupled or may be allowed to rotate to discrete positions to allow for multiple orientations of the insufflation valve relative to the remainder of the trocar housing.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 3A and 3B are enlarged isometric and exploded views, respectively, of the top cap of FIG. 2.

DETAILED DESCRIPTION

The present disclosure is related to trocar assemblies and, more particularly, to a seal assembly with latches that flex in torsion to releasably couple the seal assembly to a trocar.

The embodiments provided herein describe trocar assemblies that include a trocar and a seal cartridge configured to be releasably coupled to the trocar. The seal cartridge may include a top cap that may include a main body and a latch ring. The latch ring may include a pair of latches and may be grounded to the main body at angular positions angularly offset from the latch. Upon applying a radial load on the latches, the latch ring may be configured to flex in torsion at intermediate portions of the latch ring that angularly interpose latches and the angular positions where the latch ring is grounded to the main body.

Figure 1:
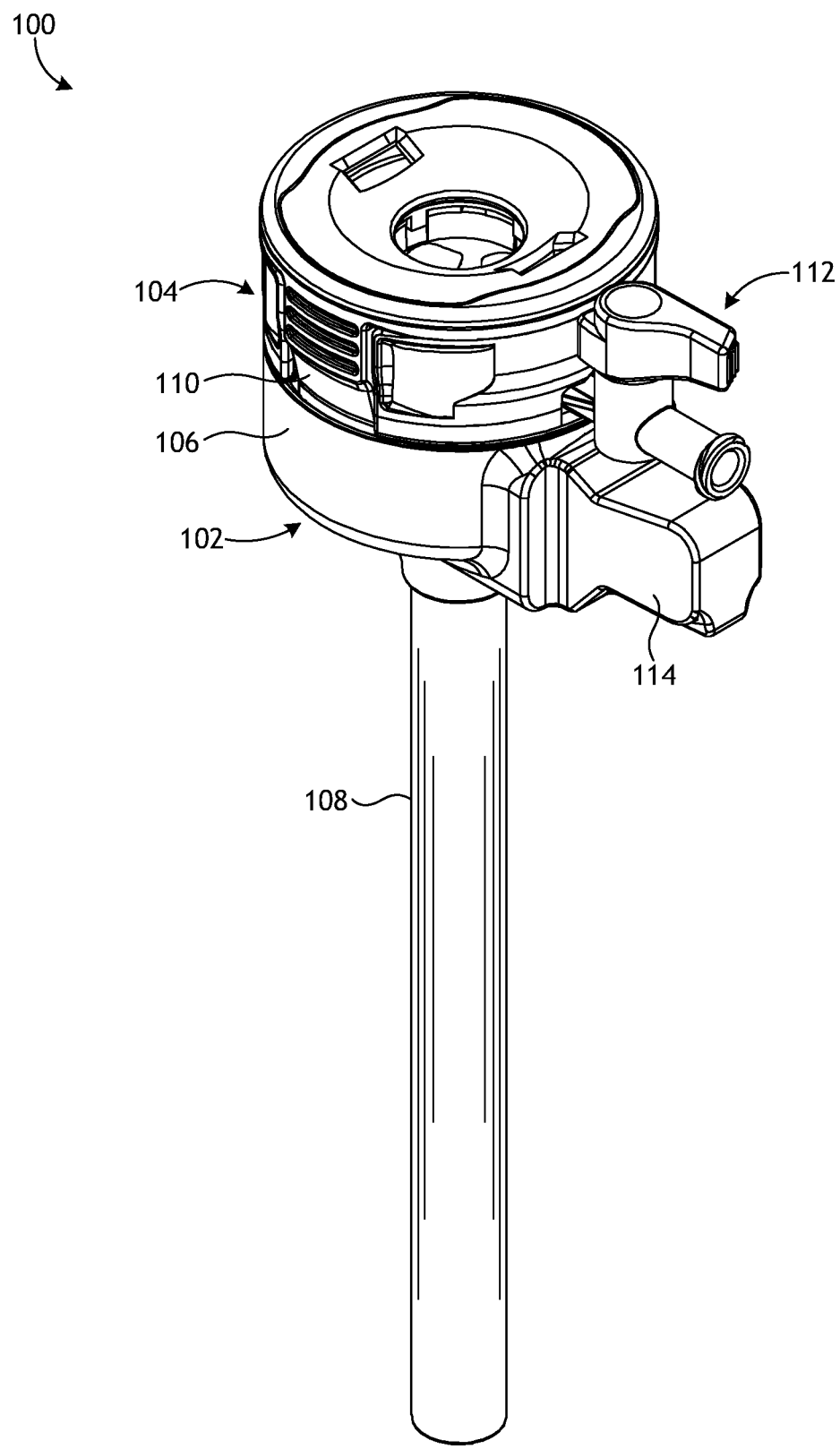
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example of a trocar assembly that can suitably incorporate the principles of the present disclosure. Those skilled in the art will readily appreciate that many alternative designs and configurations of the trocar assembly 100 may be employed or incorporated, without departing from the scope of this disclosure.

As illustrated, the trocar assembly 100 may include a trocar 102 and a seal cartridge 104 that may be releasably coupled to the trocar 102. The trocar 102 includes a trocar housing 106 and a cannula 108 that extends distally from the trocar housing 106. In some embodiments, the cannula 108 may comprise an integral extension of the trocar housing 106. In other embodiments, the trocar housing 106 and the cannula 108 may comprise two separate components that are permanently or semi-permanently mated to one another. The trocar 102 may be made of any rigid or semi-rigid material, such as a metal or a plastic.

The seal cartridge 104 may be at least partially received within the trocar housing 106 and include one or more actuatable latches 110 (one shown and one hidden) that releasably couple the seal cartridge 104 to the trocar 102. In the illustrated embodiment, the seal cartridge 104 includes two latches 110 (alternately referred to as "touchpoints") that are positioned radially (angularly) opposite each other about the circumference (outer periphery) of the seal cartridge 104. In other embodiments, more or less than two latches 110 may be employed. Moreover, the latches 110 may be equidistantly or non-equidistantly spaced from each other, without departing from the scope of the disclosure.

The trocar assembly 100 may also include an insufflation valve 112 (e.g., a stopcock valve) operable to regulate the influx of an insufflation fluid (e.g. carbon dioxide) used to elevate the interior walls of an inner body cavity (e.g., the abdomen) of a patient. In the illustrated embodiment, the insufflation valve 112 is coupled to the seal cartridge 104 or otherwise forms an integral part thereof. In other embodiments, however, the insufflation valve 112 may alternatively be coupled to the trocar housing 106 or may form an integral part thereof.

In embodiments where the trocar assembly 100 is configured to be used with a robotic system, the trocar 102 may further include a lug 114 that extends radially outward from the trocar housing 106. The robot (not shown) may be configured to latch onto the lug 114 to enable accurate insertion of surgical tools into the trocar assembly 100. In non-robotic embodiments, however, the lug 114 may be omitted, without departing from the scope of the disclosure.

Figure 2:
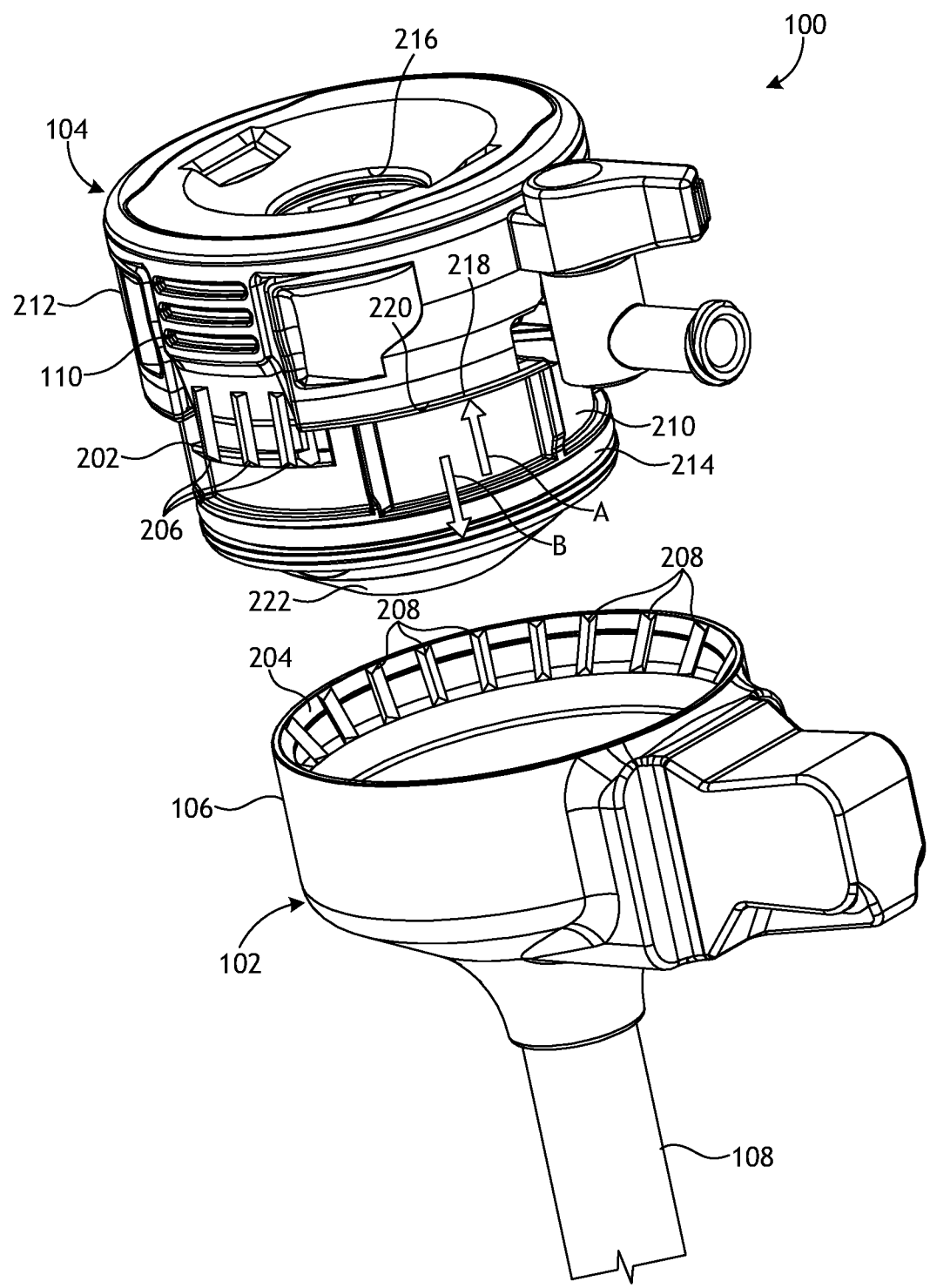
FIG. 2 is an exploded view of the trocar assembly of FIG. 1.

FIG. 2 is a partial exploded view of the trocar assembly 100 of FIG. 1. More particularly, the seal cartridge 104 is shown exploded from the trocar 102. To releasably couple the seal cartridge 104 to the trocar 102, the seal cartridge 104 may be introduced at least partially into the trocar housing 106 until the latches 110 (one shown) of the seal cartridge 104 engage and mate with the inner circumferential surface of the trocar housing 106. More specifically, each latch 110 may provide or otherwise define an outer lip 202 configured to mate with an opposing inner lip 204 defined on the inner circumferential surface of the trocar housing 106. In some embodiments, the outer lip 202 and the inner lip 204 may be oppositely angled and thereby complement one another to urge the latches 110 to flex radially inward as the outer lip 202 engages the inner lip 204 in the distal direction. Once the outer lip 202 distally traverses the inner lip 204, the latches 110 are able to flex radially outward and opposing flat surfaces of the outer lip 202 and the inner lip 204 engage to help secure and maintain the seal cartridge 104 within the trocar housing 106. To remove the seal cartridge 104, the latches 110 may be flexed radially inward to disengage the opposing flat surfaces and thereby enable to the outer lip 202 to bypass the inner lip 204 as the seal cartridge 104 is moved proximally.

In some embodiments, the inner lip 204 may extend about the entire inner circumference of the trocar housing 106. Consequently, the seal cartridge 104 may be releasably coupled to the trocar housing 106 by mating the outer lip 202 and the inner lip 204 at virtually any angular direction.

In some embodiments, the trocar assembly 100 may include an anti-rotation mechanism that helps prevent the seal cartridge 104 from rotating relative to the trocar housing 106 once properly received therein. More particularly, as illustrated, one or more protrusions 206 or "teeth" may be defined on the outer lip 202, and one or more indentations 208 may be defined on the inner lip 204. In the illustrated embodiment, a plurality of protrusions 206 and indentations 208 are defined in the outer lip 202 and the inner lip 204. Embodiments are contemplated herein, however, wherein the outer lip 202 provides only one protrusion 206 and the inner lip 204 provides only one indentation 208. In such embodiments, the seal cartridge 104 may be rotationally secured relative to the trocar 102 in a single angular orientation.

The relative spacing of the protrusions 206 may match the relative spacing of the indentations 208 such that when the seal cartridge 104 is received within the trocar housing 106 and the outer lip 202 mates with the inner lip 204, as generally described above, the protrusions 206 may be able to angularly align with and be received within the indentations 208. Receiving the protrusions 206 within the indentations 208 may help restrain the seal cartridge 104 in a particular, discrete angular orientation.

If a different angular orientation is desired, a load (e.g., a radial load) may be applied to the latches 110 to flex the latches 110 radially inward and thereby disengage the protrusions 206 from the opposing indentations 208. The seal cartridge 104 may then be rotated in either angular direction (i.e., clockwise or counter-clockwise) and the protrusions 206 will bypass the radially opposing indentations 208 until a desired angular orientation is achieved, at which point the load on the latches 110 may be released to allow the protrusions 206 to mate with opposing indentations 208 in the new angular orientation. Accordingly, in at least one embodiment, the latches 110 may be dual-purpose; to hold the seal cartridge 104 within the trocar housing 106, and to prevent rotation of the seal cartridge 104 relative to the trocar 102.

In the illustrated embodiment, the indentations 208 are defined about the entire inner circumference of the trocar housing 106 and equidistantly spaced from each other. In other embodiments, however, the indentations 208 may extend only partially about the inner circumference, without departing from the scope of the disclosure. In yet other embodiments, the indentations 208 may be defined in groups (clusters of indentations 208) arranged at predetermined intervals about the inner circumference of the trocar housing 106. In such embodiments, the groups of indentations may be equidistantly or non-equidistantly spaced from each other.

While the depicted embodiment shows the protrusions 206 being defined on the latches 110 and the indentations 208 defined on the inner surface of the trocar housing 106, an opposite configuration is contemplated herein. More specifically, in another embodiment, the protrusions 206 may be defined on the inner surface of the trocar housing 106 and the indentations 208 may be defined on the latches 110, without departing from the scope of the disclosure. In such embodiments, operation of the seal cartridge 104 with respect to the trocar 102 may be the same as generally described above.

Furthermore, while the depicted embodiment shows the protrusions 206 and the indentations 208 as elongated features that extend longitudinally and generally parallel to the centerline of the trocar assembly 100, it is contemplated herein to employ protrusions 206 and indentations 208 of a variety of shapes, sizes, and configurations. In some embodiments, for example, the protrusions 206 may comprise circular or spherical buttons and the indentations 208 may define corresponding circular or spherical cavities sized to receive the buttons. Those skilled in the art will readily appreciate that several variations of design, size, and configuration of the mating protrusions 206 and indentations 208 may be employed, without departing from the scope of the disclosure.

In some embodiments, the defined edges of one or both of the protrusions 206 and the indentations 208 may be angled or rounded. In such embodiments, as the seal cartridge 104 rotates relative to the trocar housing 106, the seal cartridge 104 may be able to "ratchet" in the angular direction as the protrusions 206 successively engage and disengage the angularly adjacent indentations 208. Having angled or rounded edges may prove advantageous in helping to facilitate easy disengagement and reengagement of the protrusions 206 with the indentations 208 during rotational movement. Moreover, in such embodiments, it may not be necessary to apply a radial load on the latches 110 to release the protrusions 206 from the opposing indentations 208. Rather, the rotational force that moves the seal cartridge 104 relative to the trocar 102 may provide sufficient force to urge the protrusions 206 to flex radially in and out of engagement with successive and radially adjacent indentations 208.

In some embodiments, the seal cartridge 104 may include two or more component parts. More particularly, the seal cartridge 104 may include a frame 210 and a top cap 212. The frame 210 may be configured to house and seat one or more seals (not shown) used to help maintain insufflation and seal about surgical tools extended longitudinally through the trocar assembly 100. The frame 210 may also include an external seal 214 that provides a sealed interface against the inside of the trocar 102 when the seal cartridge 104 is received within the trocar housing 106.

The top cap 212 may provide or otherwise define a central opening 216 that provides access into the seal cartridge 104. Surgical tools to be used in an operation may be introduced into the trocar assembly 100 via the central opening 216 and extended distally through the cannula 108. In some embodiments, the top cap 212 may be releasably coupled to the frame 210. In such embodiments, the top cap 212 may be secured to the frame 210 using a mechanical coupling, such as one or more press pins and corresponding pin cavities, one or more barbed latches and corresponding latch cavities, an interference fit, or any combination thereof. In other embodiments, the top cap 212 may be secured to the frame 210 using one or more mechanical fasteners, such as screws or rivets.

In other embodiments, however, the top cap 212 may be permanently coupled to the frame 210, such as through the use of an adhesive or via a welding operation that permanently joins the top cap 212 to the frame 210. Example welding technologies that may be employed include, but are not limited to, ultrasonic, heated tool, or any combination thereof. In yet other embodiments, the top cap 212 may be permanently coupled to the frame 210 via an infrared laser welding operation. In such embodiments, the frame 210 may be made of a material that is transparent or translucent to the wavelength of the infrared source and thereby allows the electromagnetic radiation of the infrared source to transmit through the frame 210 material with little or no dissipation. Moreover, in such embodiments, the top cap 212 may be made of a material that is opaque to and otherwise absorbs the infrared energy at the wavelength of the infrared source, and thereby absorbs or partially absorbs the electromagnetic radiation of the infrared source. In such embodiments, the frame 210 and the top cap 212 may be positioned in intimate contact with each other.

In example operation, a pulsed or continuous laser beam may be directed through a portion of the frame 210 that interfaces an opposing portion of the top cap 212, as indicated by the arrow A. In the illustrated embodiment, the laser beam A is shown directed through a radial lip or protrusion 218 defined on the frame 210, and the radial protrusion 218 interfaces with a bottom portion 220 of the top cap 212. As will be appreciated by those skilled in the art, in other embodiments, the laser beam A may be directed through other portions of the frame 210 that interface other opposing portions of the top cap 212, without departing from the scope of the disclosure.

The electromagnetic radiation of the laser transmits through the radial protrusion 218 with little or no dissipation, but is absorbed by the opposing material of the top cap 212 after transmitting through the frame 210 material. Absorbing the electromagnetic radiation with the top cap 212 material dramatically increases the temperature at the interface of the top cap 212 and the frame 210 at that location, which heats both components by thermal conduction and results in a welded interface between the two parts once cooled. This process may be repeated multiple times at various locations about the circumference of the seal cartridge 104 to secure the top cap 212 to the frame 210.

Suitable materials for the frame 210 that are transparent or translucent to the wavelength of the laser include, but are not limited to, any thermoplastic or thermoplastic composite that partially transmits infrared energy, and any combination thereof. In some embodiments the material for the frame 210 may be visibly clear, such that visible electromagnetic radiation (e.g., natural or artificial light) may pass therethrough relatively unobstructed. In other embodiments, however, the material for the frame 210 may be not be visibly clear, but instead only clear to the wavelength of the laser beam A.

Suitable materials for the top cap 212 that are generally opaque to the wavelength of the laser include, but are not limited to, any thermoplastic or thermoplastic composite that fully or partially absorbs infrared energy. Additives or coatings can be utilized to enhance the absorption properties of the material, if desired.

It is noted that while the frame 210 is described above as being made of a material that is transparent or translucent to the wavelength of the infrared source, and the top cap 212 is described as being made of a material that is opaque to and otherwise absorbs the infrared energy at the wavelength of the infrared source, it is contemplated herein to swap and still achieve the same results. In such embodiments, the top cap 212 may be made of the material that is transparent or translucent to the wavelength of the infrared source, and the frame 210 may be made of the material that is opaque to and otherwise absorbs the infrared energy at the wavelength of the infrared source.

In some embodiments, the seal cartridge 104 may further include a seal retainer 222 coupled to a distal end of the frame 210. Similar to the coupled engagement between the top cap 212 and the frame 210, in some embodiments, the seal retainer 222 may be releasably coupled to the frame 210, such as by using a mechanical coupling or with one or more mechanical fasteners, as discussed herein. The seal retainer 222 may alternatively be permanently coupled to the frame 210, such as through the use of an adhesive, ultrasonic welding, or laser welding.

In embodiments where the seal retainer 222 is laser welded to the frame 210, the frame 210 may be made of any of the materials mentioned herein that are transparent or translucent to the wavelength of a laser, and the seal retainer 222 may be made of any of the materials mentioned herein that are opaque to the wavelength of the laser. In example operation, a pulsed or continuous laser beam may be directed through a portion of the frame 210 that interfaces the seal retainer 222, as indicated by the arrow B. Similar to the process described above of laser welding the top cap 212 to the frame 210, the electromagnetic radiation of the laser B penetrates the frame 210 material with little or no dissipation, but is absorbed by the seal retainer 222 material and causes one or both of the materials to melt and provide a welded interface upon cooling. This process may be repeated multiple times at various locations about the circumference of the seal retainer 222 to secure the seal retainer 222 to the frame 210.

FIGS. 3A and 3B are enlarged isometric and exploded views, respectively, of the top cap 212, according to one or more embodiments. In some embodiments, as illustrated, the top cap 212 may include two or more component parts. More particularly, the top cap 212 may comprise a main body 302 (alternately referred to as an "upper seal retainer") and a latch ring 304 that can be mounted to the main body 302.

The main body 302 may comprise a generally cylindrical structure that defines the central opening 216. In some embodiments, the main body 302 may comprise a first portion 306a and a second portion 306b attached to or otherwise extending from the first portion 306a. In such embodiments, the main body 302 may comprise a two-shot molded component where the second portion 306b may be overmolded onto the first portion 306a, or vice versa. Moreover, in such embodiments, the first and second portions 306a,b may be made of the same or different materials. In other embodiments, however, the main body 302 may comprise a monolithic structure manufactured in a single molding process or fabricated from a single piece of material.

The main body 302 may also define slots 308 (only one visible) sized and otherwise configured to receive the latches 110 when the latch ring 304 is mounted to the main body 302. As will be appreciated, the number of slots 308 will depend on the number of latches 110. Moreover, in some embodiments, the main body 302 may further define a cutout 310 to accommodate the insufflation valve 112 (FIG. 1).

The latch ring 304 includes an annular body 312 and the latches 110 may extend distally from the annular body 312. In some embodiments, the latches 110 extend substantially perpendicular to a horizontal plane in which the annular body 312 resides. Alternatively, the latches 110 may extend at an angle offset from perpendicular to the horizontal plane in which the annular body 312 resides. The main body 302 may define an annular cutout or groove 314 sized to receive the annular body 312 when the latch ring 304 is mounted to the main body 302.

The latch ring 304 may be grounded to the main body 302 at one or more first angular (circumferential) positions 316. As used herein, the term "ground," "grounded," or any variation thereof, refers to a coupled engagement between the annular body 312 and the main body 302 that prevents the annular body 312 from flexing or moving at the particular angular position. In contrast, the latch ring 304 is not grounded to the main body 302 at one or more second angular positions 318 angularly offset from the first angular positions 316, which allows the annular body 312 to actuate at the second angular positions 318. The latches 110 and the second angular positions 318 may be considered a "rigid body" where their material is not deformed when radially actuated.

In the illustrated embodiment, the latch ring 304 may be grounded to the main body 302 at two first angular positions 316 arranged angularly opposite each other (i.e., at or about 180° offset). The latches 110 may be provided at the second angular positions 318 and angularly interpose the first angular positions 316, such as being 90° offset from the first angular positions 316. In other embodiments, however, only one first angular position 316 and one second angular position 318 may be defined on the latch ring 304, without departing from the scope of the disclosure.

The latch ring 304 may be grounded to the main body 302 at the first angular positions 316 via a variety of means or processes. In some embodiments, for example, the latch ring 304 may be permanently grounded to the main body 302 at the first angular positions 316 using, for example, an adhesive, ultrasonic welding, laser welding, one or more permanent mechanical attachment features, or any combination thereof. In other embodiments, however, the latch ring 304 may be semi-permanently or releasably grounded to the main body 302 at the first angular positions 316. In such embodiments, the latch ring 304 may be coupled to the main body 302 using, for example, one or more mechanical fasteners (e.g., screws, rivets, pins, etc.), an interference fit, a shrink fit, a bayonet fitting, one or more non-permanent mechanical fasteners (e.g., latches, snaps, etc.), or any combination thereof.

In the illustrated embodiment, the latch ring 304 may be releasably (or semi-permanently) coupled to the main body 302. More particularly, and with reference to FIG. 3B, the latch ring 304 may provide or otherwise define one or more press pins 320 that extend distally from the annular body 312, and the main body 302 may provide or otherwise define one or more corresponding apertures 322 sized to receive the press pins 320. The latch ring 304 may be mounted to the main body 302 by angularly aligning the press pins 320 with the apertures 322 and receiving the press pins 320 into the corresponding apertures 322 via, for example, an interference fit.

In the illustrated embodiment, two groups (clusters) of press pins 320 are provided by the latch ring 304, and two corresponding groups (clusters) of apertures 322 are provided by the main body 302. While two press pins 320 and two corresponding apertures 322 are depicted in each group (cluster), it will be appreciated that more or less than two press pins 320 and apertures 322 may be employed, without departing from the scope of the disclosure.

The two groups are arranged angularly opposite each other at the first angular positions 316, and the latches 110 interpose the two groups at the second angular positions 318. Receiving the press pins 320 into the apertures 322 effectively grounds the latch ring 304 at the first angular positions 316 such that the annular body 312 is unable to flex or move at those locations. In contrast, the latch ring 304 is not grounded to the main body 302 at the second angular positions 318, which allows the annular body 312 to actuate at those locations when the latches 110 are actuated.

The latches 110 may be actuated by applying a radial load to the latches 110 in opposing radially inward directions toward the centerline. The radial load may be applied manually by a user (e.g., pinching between the index finger and the thumb) or by a robotic actuator. The radial load urges the latches 110 to rotate radially inward relative to the main body 302 at the slots 308, which causes intermediate portions 324 of the latch ring 304 to bend (flex) in torsion. The intermediate portions 324 comprise arcuate sections (segments) of the annular body 312 that angularly interpose the first and second angular positions 316, 318 and are, therefore, located at intermediate angular positions on either angular side of the latches 110.

The intermediate portions 324 may be characterized as "living hinges" that flex in torsion when the latches 110 are actuated, and elastically return to a relaxed state when the radial load on the latches 110 is removed. As illustrated, the latches 110 may transition to the intermediate portions 324 at a radius 326 defined in the annular body 312 on either angular side of the latches 110. The radius 326 at each corner may prove advantageous in converting the radial load applied to the latches 110 to a torsional load assumed at the intermediate portions 324. Moreover, the radii 326 may also allow the intermediate portions 324 to twist without binding against the main body 302.

The cross-sectional shape and area of the intermediate portions 324 may be varied and otherwise optimized to provide an ideal spring rate and touchpoint tactile feedback for the latches 110. As will be appreciated, the cross-sectional shape and area of the intermediate portions 324 may dictate the amount of torsion needed to release the latches 110. In some embodiments, the cross-sectional shape and area of the annular body 314 at the intermediate portions 324 may be different than the cross-sectional shape and area of the annular body 314 at one or both of the first and second angular positions 316, 318 to promote and control torsion through this area.

Figure 4A:
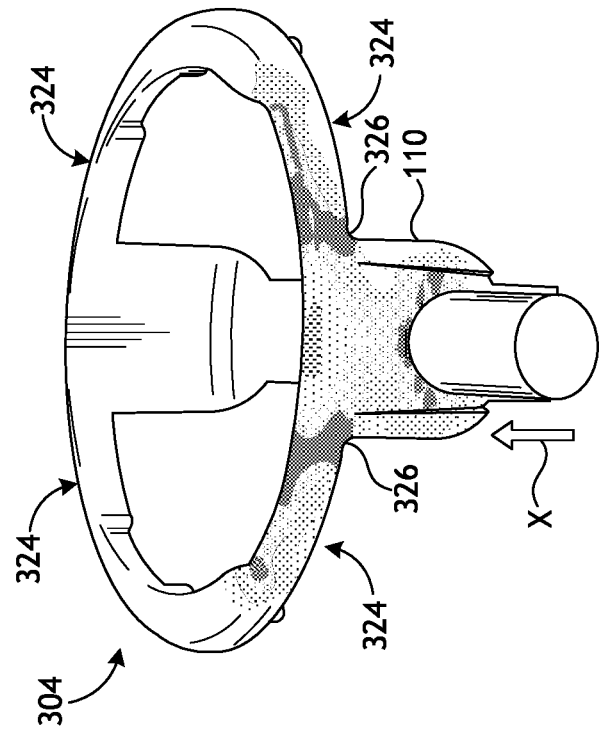
FIGS. 4A and 4B are isometric views of the latch ring of FIGS. 3A-3B depicting example actuation.
Figure 4B:
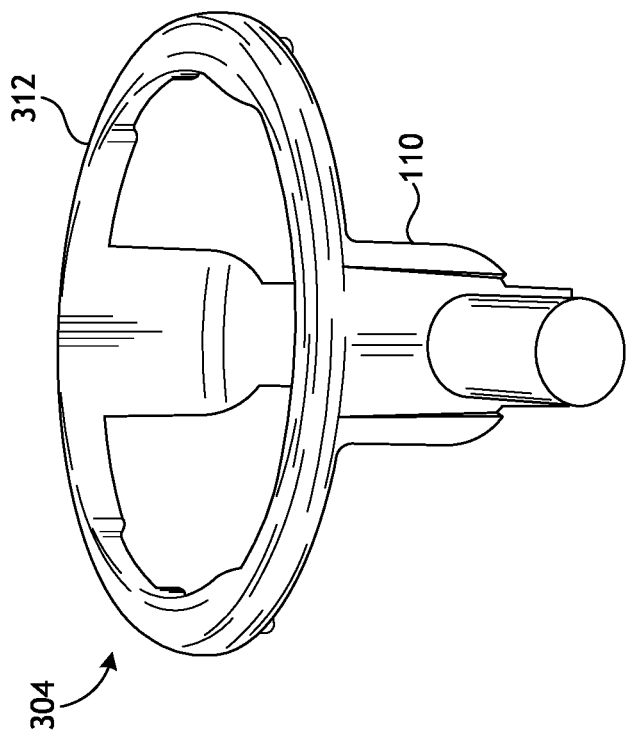

FIGS. 4A and 4B are isometric views of the latch ring 304 of FIGS. 3A-3B depicting example actuation. More specifically, FIGS. 4A and 4B depict finite element analysis (FEA) results from applying a radial load on one of the hinges 110, as indicated by the arrow X (FIG. 4B). FIG. 4A shows the latch ring 304 in its relaxed state and, thus, no FEA data is obtained. In contrast, FIG. 4B shows the latch ring 304 with the radial load X applied on the latch 110, and the FEA data shows strain building in the intermediate portions 324 of the annular body 312. Pockets of strain are especially evident at the radii 326, where the latch 110 joins the annular body 312 and structurally converts the radial load X to torsion loading assumed at the intermediate portions 324. The FEA results indicate that the latch ring 304 twists about itself in torsion at the intermediate portions 324 as the latch 110 is being depressed.

Conventional latches for seal cartridges typically operate as a cantilever beam that bends linearly when a radial load is applied. In contrast, the presently-described latch ring 304 does not bend linearly, but rather twists around on itself to facilitate linear movement at the latch 110. The material of the latch ring 304 comes under torsion instead of under a bending strain. Due to the minimal space required, the torsional actuation of the latch ring 304 may be advantageous over conventional linearly bending latches that require more space or compromise in the force to actuate at the latch 110.

Embodiments disclosed herein include:

A. A trocar assembly that includes a trocar, and a seal cartridge configured to be releasably coupled to the trocar and including a top cap that includes a main body and a latch ring, wherein the latch ring is grounded to the main body at a first angular position and has a latch located at a second angular position angularly offset from the first angular position, and wherein applying a radial load on the latch causes the latch ring to flex in torsion at an intermediate portion that angularly interposes the first and second angular positions.

B. A seal cartridge for a trocar assembly that includes a frame that houses one or more seals, and a top cap coupled to the frame and including a main body and a latch ring, wherein the latch ring is grounded to the main body at a first angular position and has a latch located at a second angular position angularly offset from the first angular position, and wherein applying a radial load on the latch causes the latch ring to flex in torsion at an intermediate portion that angularly interposes the first and second angular positions.

C. A method of using a trocar assembly that includes receiving a seal cartridge at least partially into a trocar housing of a trocar, the seal cartridge including a top cap that includes a main body and a latch ring, wherein the latch ring is grounded to the main body at a first angular position and has a latch located at a second angular position angularly offset from the first angular position, and applying a radial load on the latch and thereby causing the latch ring to flex in torsion at an intermediate portion that angularly interposes the first and second angular positions.

Each of embodiments A, B, and C may have one or more of the following additional elements in any combination: Element 1: wherein the latch comprises a first latch and the latch ring is grounded to the main body at two first angular positions located angularly opposite each other, the latch ring further including a second latch located angularly opposite the first latch and the first and second latches angularly interpose the two first angular positions. Element 2: wherein the radial load is applied on the first and second latches simultaneously in opposite radial directions. Element 3: wherein the latch transitions to the intermediate portion at a radius defined in the latch ring. Element 4: wherein a cross-sectional shape and area of the intermediate portion is different from a cross-sectional shape and area of the latch ring at one or both of the first and second angular positions to promote and control local torsion in the intermediate portion. Element 5: wherein the latch ring is permanently grounded to the main body at the first angular position. Element 6: wherein the latch ring is releasably grounded to the main body at the first angular position. Element 7: wherein the trocar includes a trocar housing and a cannula that extends distally from the trocar housing, the trocar assembly further comprising an inner lip defined on an inner circumferential surface of the trocar housing, an outer lip defined by the latch and matable with the inner lip to releasably couple the seal cartridge to the trocar, one or more indentations defined on one of the inner and outer lips, and one or more protrusions defined on the other of the inner and outer lips, wherein the one or more protrusions are receivable within the one or more indentations to prevent the seal cartridge from rotating relative to the trocar housing. Element 8: wherein edges of one or both of the one or more protrusions and the one or more indentations are angled or rounded.

Element 9: further comprising one or more press pins defined by the latch ring at the first angular position, and one or more apertures defined by the main body at the first angular position to receive the one or more press pins and thereby ground the latch ring to the main body. Element 10: wherein the latch comprises a first latch and the latch ring is grounded to the main body at two first angular positions located angularly opposite each other, the latch ring further including a second latch located angularly opposite the first latch and the first and second latches angularly interpose the two first angular positions. Element 11: wherein the main body defines slots that receive the first and second latches when the latch ring is mounted to the main body. Element 12: wherein the latch transitions to the intermediate portion at a radius defined in the latch ring. Element 13: wherein a cross-sectional shape and area of the intermediate portion is different from a cross-sectional shape and area of the latch ring at one or both of the first and second angular positions to promote and control local torsion in the intermediate portion.

Element 14: wherein the latch comprises a first latch and the latch ring is grounded to the main body at two first angular positions located angularly opposite each other, the latch ring further including a second latch located angularly opposite the first latch such that the first and second latches angularly interpose the two first angular positions, and wherein applying the radial load on the latch comprises applying the radial load on the first and second latches simultaneously in opposite radial directions, and causing the latch ring to flex in torsion at intermediate portions that angularly interpose the first and second latches and the two first angular positions. Element 15: further comprising converting the radial load to a torsional load at a radius defined in the latch ring wherein the latch transitions to the intermediate portion. Element 16: wherein an inner lip is defined on an inner circumferential surface of the trocar housing and an outer lip is defined by the latch and matable with the inner lip to releasably couple the seal cartridge to the trocar, and wherein receiving the seal cartridge at least partially into the trocar housing comprises mating one or more protrusions defined on one of the inner and outer lips with one or more indentations defined on the other of the inner and outer lips, and preventing the seal cartridge from rotating relative to the trocar housing when the one or more protrusions are mated with the one or more indentations. Element 17: wherein applying the radial load on the latch further comprises disengaging the one or more protrusions from the one or more indentations, and rotating the seal cartridge relative to the trocar housing.

By way of non-limiting example, exemplary combinations applicable to A, B, and C include: Element 1 with Element 2; Element 7 with Element 8; Element 10 with Element 11; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
    a trocar including a trocar housing and a cannula extending from the trocar housing;
    a seal cartridge at least partially received within the trocar housing and providing one or more latches that releasably couple the seal cartridge to the trocar housing, wherein each latch provides an outer lip matable with an opposing inner lip defined on an inner circumferential surface of the trocar housing; and
    an anti-rotation mechanism provided at an interface between the trocar housing and the seal cartridge to prevent the seal cartridge from rotating relative to the trocar housing once received therein, the anti-rotation mechanism including:
    one or more indentations defined on one of the inner and outer lips, and
    one or more protrusions defined on the other of the inner and outer lips,
    wherein the one or more protrusions are receivable within the one or more indentations to prevent the seal cartridge from rotating relative to the trocar housing.

2. The trocar assembly of claim 1, wherein the outer lip and the inner lip are oppositely angled and complement one another to urge the one or more latches to flex radially inward as the outer lip engages the inner lip.

3. The trocar assembly of claim 1, wherein the inner lip extends about the entire inner circumference of the trocar housing.

4. The trocar assembly of claim 1, wherein the seal cartridge is rotatable relative to the trocar housing by applying a radial load on the one or more latches and thereby releasing the one or more protrusions from the one or more indentations.

5. The trocar assembly of claim 1, wherein edges of one or both of the one or more protrusions and the one or more indentations are angled or rounded.

6. The trocar assembly of claim 1, wherein the one or more indentations or the one or more protrusions are defined about the entire inner circumference of the trocar housing.

7. The trocar assembly of claim 1, further comprising an external seal arranged on the seal cartridge to seal against an inside portion of the trocar housing when the seal cartridge is received therein.

8. The trocar assembly of claim 1, wherein the seal cartridge includes a top cap comprising a main body and a latch ring grounded to the main body at one or more first angular positions,
    wherein the one or more latches comprise first and second latches located at corresponding second angular positions angularly offset from the one or more first angular positions, and
    wherein applying a radial load on the latch causes the latch ring to flex in torsion at an intermediate portion that angularly interposes each first and second angular position.

9. The trocar assembly of claim 1, wherein the one or more latches are positioned radially about an outer circumference of the seal cartridge.

10. A method of assembling a trocar assembly, comprising:
    receiving a seal cartridge at least partially into a trocar housing of a trocar;
    releasably coupling the seal cartridge to the trocar housing by mating one or more latches provided on the seal cartridge with the trocar housing;
    preventing the seal cartridge from rotating relative to the trocar housing with an anti-rotation mechanism provided at an interface between the trocar housing and the seal cartridge; and
    generating a sealed interface at an interface between the seal cartridge and an inside portion of the trocar housing with an external seal provided on a radial surface of the seal cartridge when the seal cartridge is received within the trocar housing.

11. The method of claim 10, wherein each latch provides an outer lip matable with an opposing inner lip defined on an inner circumferential surface of the trocar housing, the method further comprising urging the one or more latches to flex radially inward as the outer lip engages the inner lip as the seal cartridge advances in a distal direction.

12. The method of claim 11, wherein the anti-rotation mechanism includes one or more indentations defined on one of the inner and outer lips, and one or more protrusions defined on the other of the inner and outer lips, and wherein preventing the seal cartridge from rotating relative to the trocar housing comprises:
    receiving the one or more protrusions within the one or more indentations; and preventing the seal cartridge from rotating relative to the trocar housing with the one or more protrusions engaged against the one or more indentations.

13. The method of claim 12, further comprising:
applying a radial load on the one or more latches and thereby releasing the one or more protrusions from the one or more indentations; and
rotating the seal cartridge relative to the trocar housing when the one or more protrusions are disengaged from the one or more indentations.

14. The method of claim 12, wherein edges of one or both of the one or more protrusions and the one or more indentations are angled or rounded, the method further comprising:
rotating the seal cartridge relative to the trocar housing; and
ratcheting the one or more protrusions across the one or more indentations as the seal cartridge rotates relative to the trocar housing.

15. The method of claim 10, wherein the one or more latches comprise first and second latches arranged angularly opposite each other, the method further comprising:
applying a radial load on the first and second latches in opposing radial directions and thereby disengaging the anti-rotation mechanism; and
rotating the seal cartridge relative to the trocar housing with the anti-rotation mechanism disengaged.

16. The method of claim 11, wherein the inner lip extends about the entire inner circumference of the trocar housing.

17. The method of claim 10, wherein the one or more latches comprise first and second latches arranged angularly opposite each other, the method further comprising:
applying a radial load on the first and second latches in opposing radial directions and thereby disengaging the outer lip with the opposing inner lip; and
removing the seal cartridge from the trocar housing.

18. The method of claim 10, wherein the seal cartridge includes a top cap that comprises a main body and a latch ring grounded to the main body at a first angular position, the one or more latches being located at corresponding second angular positions angularly offset from the first angular position, the method further comprising:
applying a radial load on the one or more latches and thereby causing the latch ring to flex in torsion at an intermediate portion that angularly interposes the first and second angular positions.

19. The method of claim 18, further comprising converting the radial load to a torsional load via a radius defined in the latch ring, wherein the radius defines the transition from the one or more latches to the intermediate portion.

20. The trocar assembly of claim 10, wherein the one or more latches are positioned radially about an outer circumference of the seal cartridge.

* * * * *